(12) United States Patent
Liu et al.

(10) Patent No.: US 8,673,604 B1
(45) Date of Patent: Mar. 18, 2014

(54) *CLAVISPORA* SPP. STRAIN

(75) Inventors: Zonglin L. Liu, Peoria, IL (US); Scott A. Weber, Washington, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/482,309

(22) Filed: May 29, 2012

(51) Int. Cl.
*C12P 7/14* (2006.01)

(52) U.S. Cl.
USPC ............................................. 435/162

(58) Field of Classification Search
None
See application file for complete search history.

(56) References Cited

PUBLICATIONS

Liu et al., "A new Beta-glucosidase producing yeast for lower-cost cellulosic ethanol production from xylose-extracted corncob residues by simultaneous saccharification and fermentation", Bioresource Technology, 2012, vol. 104, pp. 410-416.*

\* cited by examiner

*Primary Examiner* — Suzanne M Noakes
(74) *Attorney, Agent, or Firm* — John D. Fado; Albert Y. Tsui; Lesley Shaw

(57) ABSTRACT

Disclosed is a novel *Clavispora* spp. yeast strain, NRRL Y-50464, that produces ethanol. More specifically, the yeast strain is able to utilize cellobiose as a sole carbon source and produce native β-glucosidase enzyme activity under a one-step simultaneous saccharification and fermentation of cellulose to ethanol.

13 Claims, 8 Drawing Sheets

US 8,673,604 B1

CLAVISPORA SPP. STRAIN

FIELD OF INVENTION

The present invention is for a novel *Clavispora* spp. yeast strain, NRRL Y-50464, that produces ethanol. More specifically, the yeast strain is able to utilize cellobiose as a sole carbon source and produce native β-glucosidase enzyme activity under a one-step simultaneous saccharification and fermentation of cellulose to ethanol.

BACKGROUND OF INVENTION

Over 90% of ethanol biofuel produced in the United States is made from corn starch using *Saccharomyces* strains to ferment the glucose obtained by hydrolysis of the starch. The United States Environmental Protection Agency has revised the Renewable Fuel Standard (RFS) program as required by the Energy Independence and Security Act of 2007 (EISA). The final rule (RFS2) increases the volume requirements for total renewable fuel to 20.5 billion gallons and for cellulosic biofuel to 3.0 billion gallons by 2015. To meet these mandates, it will be necessary to use cellulosic biomass, an abundant and renewable carbon source, as a feedstock. However, the microbial strains used to ferment the glucose released by hydrolysis of starch are not capable of fermenting the more diverse mixture of sugars released by hydrolysis of lignocellulosic biomass.

The necessary deconstruction of cellulosic polymers, enzymatic hydrolysis, and saccharification require additional processing procedures to use lignocellulosic biomass ultimately increases the cost of lignocellulose to ethanol conversion when compared to current starch-to-ethanol technologies. Reducing the cost of cellulosic ethanol production poses significant challenges both in scientific advances and technological development.

One barrier is that yeast strains are generally capable of fermenting the hexose sugars, glucose and galactose; however, they do not naturally ferment the pentose sugars, xylose or arabinose without any genetic modification.

Corncobs are commonly used for xylose production, and xylose-extracted corncob residue (X-ER) is an abundant byproduct after industrial processing (Zhang et al., 2011). The X-ER contains a significant amount of cellulose and is a potential feedstock for cellulosic ethanol production. However, ideal processing procedures and economic cellulosic ethanol production from X-ER have not been achieved yet on a large scale (Zhang et al., 2011). More efficient, lower-cost, and consolidated processing procedures are needed.

Simultaneous saccharification and fermentation (SSF) using cellobiose fermenting yeast *Brettanoinyces custersii*, is described in U.S. Pat. No. 5,100,791, by Spindler, et al. In a simultaneous saccharification fermentation process, saccharification involves the breakdown of cellulose into simpler sugars by a cellulase enzyme. One such sugar is cellobiose, a sugar comprised of two glucose molecules that is subsequently broken down into glucose. The cellulase enzyme will typically have an insufficient amount of β-glucosidase, which is the part of the cellulase enzyme that can breakdown cellobiose into glucose. Cellobiose inhibits the endo- and exo-glucanase enzymes, and this retards the overall ethanol production rate and yield in a simultaneous saccharification fermentation process.

Since the commonly used ethanologenic yeast *Saccharomyces cerevisiae* is unable to utilize cellobiose, β-glucosidase is added to digest cellobiose into glucose in order to be utilized by the fermentation ethanologenic yeast.

Enzymes are one of the major costs of cellulosic ethanol production (Piccolo and Bezzo, 2009). In addition, efficient enzymatic saccharification requires a higher temperature while microbial growth and fermentation function optimally at a lower temperature. Furthermore, inhibitory compounds such as representative 2-furaldehyde (furfural) and 5-(hydroxymethyl)-2-furaldehyde (HMF) are often generated during biomass pretreatments such as commonly used dilute acid pretreatment, that interfere with microbial growth and fermentation (Palmquist and Hahn-Hagerdal, 2000; Liu and Blaschek, 2010). These undesirable elements and redundant processing procedures compromise the efficiency of SSF.

There is a need in the art to develop an ethanologenic yeast strain that is tolerant to both a higher temperature and inhibitors commonly encountered in the SSF. This new yeast produces sufficient native β-glucosidase enzyme activity allowing it to grow on cellobiose as sole source of carbon. Thus, no additional β-glucosidase enzyme needs to be added for cellulosic ethanol conversion from X-ER by SSF. Development of this yeast provides potential consolidated bio-processing means for lower-cost cellulosic ethanol production from industrial byproduct of xylose extracted corncobs and other lignocellulosic biomass materials.

BRIEF DESCRIPTION OF THE DRAWINGS

The present invention together with the above and other objects and advantages may best be understood from the following detailed description of the embodiment of the invention illustrated in the drawings.

FIG. 5A depicts a 25% solid loading of xylose-extracted corncob residues by simultaneous saccharification and fermentation using 2-L bioreactors, while FIG. 5B depicts a 25% solid loading of xylose-extracted corncob. Ethanol is labeled by open squares; cellobiose, filled squares; and glucose, filled circles.

DEPOSIT OF BIOLOGICAL MATERIAL

Figure 1A:
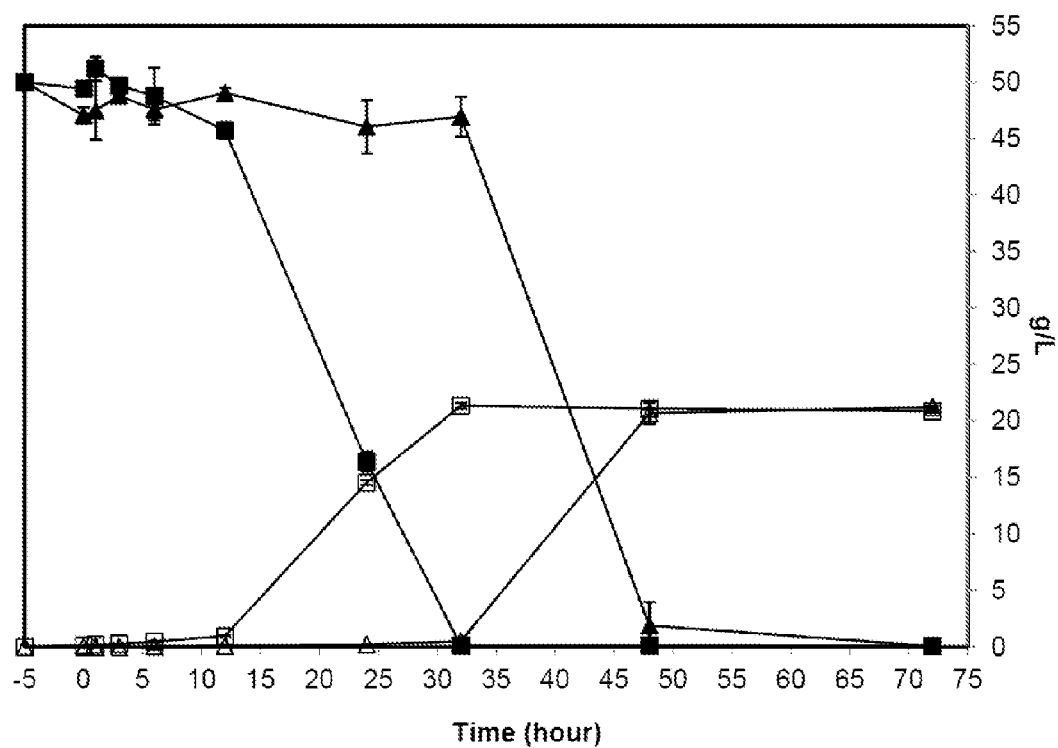
FIG. 1A is a graph depicting corresponding ethanol production (open symbols) and glucose consumption (filled symbols) for Y-50464 (squares) and Y-417 (triangles).

Strain Y-50464 is identified as a *Clavispora* yeast based on variable nucleotide tandem repeat (VNTR) analysis. NRRL Y-50464 was deposited on Feb. 10, 2011, under the provisions of the Budapest Treaty in the Agricultural Research Culture Collection (NRRL) in Peoria, Ill.

The subject culture has been deposited under conditions that assure that access to the culture will be available during the pendency of this patent application to one determined by the Commissioner of Patents and Trademarks to be entitled thereto under 37 CFR §1.14 and 35 USC §122. The deposits are available as required by foreign patent laws in countries wherein counterparts of the subject application, or its progeny, are filed. However, it should be understood that the availability of the deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., the culture will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing them.

DEFINITIONS

In a simultaneous saccharification fermentation process, saccharification involves the breakdown of cellulose into simpler sugars by a cellulase enzyme. One such sugar is cellobiose, a sugar comprised of two glucose molecules that is subsequently broken down into glucose by the enzyme beta-glucosidase. Beta-glucosidase is added to a fermentation batch—provided that the yeast used in the fermentation process cannot endogenously produce beta-glucosidase.

The term "beta-glucosidase" or "β-glucosidase" is defined herein as a beta-D-glucoside glucohydrolase (E.C. 3.2.1.21), which catalyzes the hydrolysis of terminal nonreducing beta-D-glucose residues with the release of beta-D-glucose. For purposes of the present invention, beta-glucosidase activity is determined according to the basic procedure described Grover et al., 1977, Biophysica Acta, 482, 89-108; Saha et al., 2008, J. Biobased Mater. Bioenergy 2, 210-217).

As used herein, one unit of "beta-glucosidase activity" is defined by one unit of enzyme needed to release 1 µmole of p-nitrophenol per min under the defined conditions. Moreover, beta-glucosidase activity was assayed on a 96-well microtiter plate. Briefly, 100 µl of 5 mM p-nitrophenyl β-D-glucoside in 100 mM citrate buffer at pH 5.5 was pipetted in each well. Then 25 µl of crude or purified enzyme prep was added to each sample to start the reaction. The reaction was carried out in an incubator at 45° C. for 30 min. After incubation, 125 µl ice cold 0.5 M $Na_2CO_3$ was added to stop each reaction and the absorbance at 405 nm measured using a plate reader Power Wavex 340 (Bio-Tek Instruments Inc., Winooski, Vt.). Other names for beta-glucosidase enzyme activity include: gentiobiase; cellobiase; emulsin; elaterase; aryl-β-glucosidase; β-D-glucosidase; β-glucoside glucohydrolase; arbutinase; amygdalinase; p-nitrophenyl β-glucosidase; primeverosidase; amygdalase; limarase; salicilinase; and β-1,4-glucosidase.

The terms "culturing" or "cultivation" refer to growing a population of microbial cells under suitable conditions in a liquid or solid medium:

The term "xylose-extracted corncob residue" or "X-ER" refers to corncob residue that have been treated via acid hydrolysis to release xylose, cellulose, and lignin. Typically, the residue has been treated with 1.2 to 1.5% $H_2SO_4$ at 125° C. to minimize the production of inhibitory compounds such as furan and 5-hydroxymethylfurfural.

Disclosed herein is an isolated *Clavispora* spp. having been deposited with the United States Department of Agriculture, Agricultural Research Patent Culture Collection as Accession Deposit Number NRRL Y-50464. In one embodiment of the invention, the *Clavispora* spp. strain NRRL Y-50464 metabolizes cellobiose and produces ethanol. In another embodiment of the invention, *Clavispora* spp. strain NRRL Y-50464 produces beta-glucosidase under when fermenting cellobiose.

Also disclosed is a method of producing ethanol from the fermentation of cellulosic material, the method comprising fermenting *Clavispora* spp. strain NRRL Y-50464 with cellulosic material under suitable conditions for a period of time sufficient to allow fermentation of at least a portion of cellulosic material to ethanol. In one embodiment of the invention, β-glucosidase produced by *Clavispora* spp. strain NRRL Y-50464 and cellulase are added to the cellulosic material simultaneously for simultaneous saccharification and fermentation. In another embodiment of the invention the cellulosic material comprises a lignocellulosic biomass.

In yet another embodiment of the invention, the lignocellulosic biomass is subjected to a pretreatment to increase the accessible surface area of cellulose, prior to said contact with said β-glucosidase and said cellulase. In another embodiment of the invention, pretreatment is selected from the group consisting of treatment with acid, treatment with alkali, ammonia fiber explosion, treatment with an organic solvent, autohydrolysis by steam explosion, acid steam treatment, treatment with hot, compressed liquid water, pressure cooking, milling, grinding, shearing, and extruding. In another embodiment of the invention, the lignocellulosic material is selected from the group consisting of agricultural residues, wood, municipal solid wastes, paper and pulp industry wastes, and herbaceous crops.

Disclosed herein is a method of producing ethanol from the fermentation of cellulosic material, the method comprising fermenting *Clavispora* spp. strain NRRL Y-50464 with glucose. In one embodiment of the invention, the conversion of said cellulosic material to glucose and the fermentation of glucose to ethanol are conducted simultaneously. In another embodiment of the invention, the conversion of said cellulosic material to glucose and the fermentation of glucose to ethanol are conducted sequentially.

DETAILED DESCRIPTION OF THE INVENTION

Disclosed herein is an isolated *Clavispora* spp. having been deposited with the United States Department of Agriculture, Agricultural Research Patent Culture Collection as Accession Deposit Number NRRL Y-50464. Strain Y-50464 was derived from a parent strain and the parent strain is designed Y-417 herein. *S. cerevisiae* NRRL Y-12632 from the ARS Culture Collection was also used as a comparison yeast study. Cell cultures were maintained and pre-cultured on YP media consisting of 50 g glucose, 3.0 g yeast extract, 5.0 g Peptone.

Analysis by high performance liquid chromatography (HPLC) as detailed in the examples was conducted using a Shimadzu LC-20AD (Shimadzu Corporation, Kyoto, Japan) equipped with an HPX-87H Aminex ion exclusion column (Bio-Rad, Hercules, Calif.) kept at 65° C. Sugar consumption and ethanol production were detected using a Shimadzu RID-10A Refractive index detector while furfural and HMF and their conversion products were detected using a Shimadzu SPD-m20A PDA. Samples were run isocratically using 0.0017N H2SO4 as mobile phase at a flow rate of 0.6 mL/min.

Strain Identification

An ethanologenic yeast strain affiliated with sweet sorghum was isolated and examined by sequence of 26S ribosomal RNA gene as previously described by Kurtzman et al., 1998, Anton. Leeuw. 73, 331-371. Based on comparison of NCBI DNA sequence database (www.ncbi.nlm.nih.gov) it was identified as a strain of *Clavispora* sp. and designated as Y-417. A laboratory adaptation using evolutionary engineering was performed to obtain an inhibitor-tolerant and thermotolerant strain that can grow rapidly at 37° C. using procedures similar as previously described in Liu et al., 2005, where pressure and temperature conditions were increase to apply selection pressure. The newly adapted tolerant yeast strain was designated as NRRL Y-50464.

Example 1

Cell Growth of Y-50464 on Cellobiose as Sole Carbon Source

A comparison of growth on cellobiose as sole source of carbon was performed between strains Y-50464 and *S. cerevisiae* Y-12632. A 100-ml Nalgene culture bottle was filled with 50 ml of YP media amended with 5% cellobiose. Each culture was inoculated with a pre-culture at a starting OD(600 nm) reading of 0.03 and incubated with agitation for 48 h. The lid of Nalgene bottles was kept tight to allow for minimal air exchange. Samples were taken for OD(600 nm) reading over the course of growth. The experiment was carried out in triplicate.

On a medium containing 5% cellobiose as sole carbon source, strain Y-50464 quickly established a culture at 37° C. and the cell growth reached to a stationary phase in no more than 24 h. In contrast, strain Y-12632 of *S. cerevisiae* at its optimum growth temperature of 30° C., was unable to grow on cellobiose. The minimum background of the OD reading observed was likely attributed to residue C-6 sugars in the medium.

Example 2

Beta-Glucosidase Enzyme Activities

Yeast strains Y-50464 and Y-12632 were grown on 250 ml of YP media with either 5% glucose or 5% cellobiose as a carbon source with a 2% inoculum from an overnight culture. The cultures were incubated with agitation at 225 rpm at 37° C. for strain Y-50464 and 30° C. for strain Y-12632. After 17 h, cells were harvested and lysed using Y-PER plus, dialyzable yeast protein extraction reagent (Thermo Scientific, Rockford, Ill.) following manufacturer's instructions. The supernatant for each sample was then diluted 1,000 times and used as crude enzyme prep for enzyme assays.

When Y-50464 was grown on cellobiose as sole source of carbon as detailed in Example 1, a large amount of β-glucosidase activity was observed in crude cell protein extracts by in vitro assay (Table 1). This enzyme activity was also observed when Y-50464 was grown on glucose but at a considerably lower level. In contrast, strain Y-12632 of *S. cerevisiae* produced no detectable β-glucosidase activity induced by either sugar.

TABLE 1

Beta-glucosidase activity as measured by in vitro assay using crude cell protein extracts 17 h after incubation.

| Strain | Carbon source | Total protein (mg) | Total unit (U) | Specific activity (U/mg/ml) |
|---|---|---|---|---|
| Y-50464 | Cellobiose | 221.1 ± 35.4 | 264.5 ± 29.5 | 1.20 |
|  | Glucose | 244.4 ± 2.5 | 41.6 ± 0.9 | 0.17 |
| Y-12632 | Cellobiose | 182.8 ± 1.2 | na* | na |
|  | Glucose | 196.0 ± 16.2 | na | na |

*na, no detectable activity.

Example 3

Tolerance to Inhibitors

Strain Y-50464, as an adapted mutant, is able to grow rapidly at 37° C. compared with its parental strain Y-417 at 30° C. Cell growth in media containing 15 mM each of furfural and HMF was evaluated on 200 ml YP+ medium using a fleaker system as previously described in Liu et al., 2005, Appl. Biochem. Biotechnol. 121-124, 451-460 and incorporated herein by reference. Cultures were inoculated using an overnight culture to an OD(600 nm) reading at 0.05 at the optimal growth temperature for each strain. Cultures were incubated with agitation at 250 rpm. After 5 h incubation, furfural and HMF were added to the media at a final concentration of 15 mM each. The time point of the inhibitor addition was designated as 0 h. Samples were taken periodically and frozen at −20° C. until use for HPLC analysis.

All chemicals including furfural and HMF were obtained from Sigma-Aldrich (St. Louis, Mo.). HMF conversion product 2,5-bis-hydroxymethylfuran (furandimethanol, FDM) was synthesized as previously described in Liu et al., 2008, Appl. Microbiol. Biotechnol. 81, 743-753 and incorporated herein by reference.

Figure 1B:
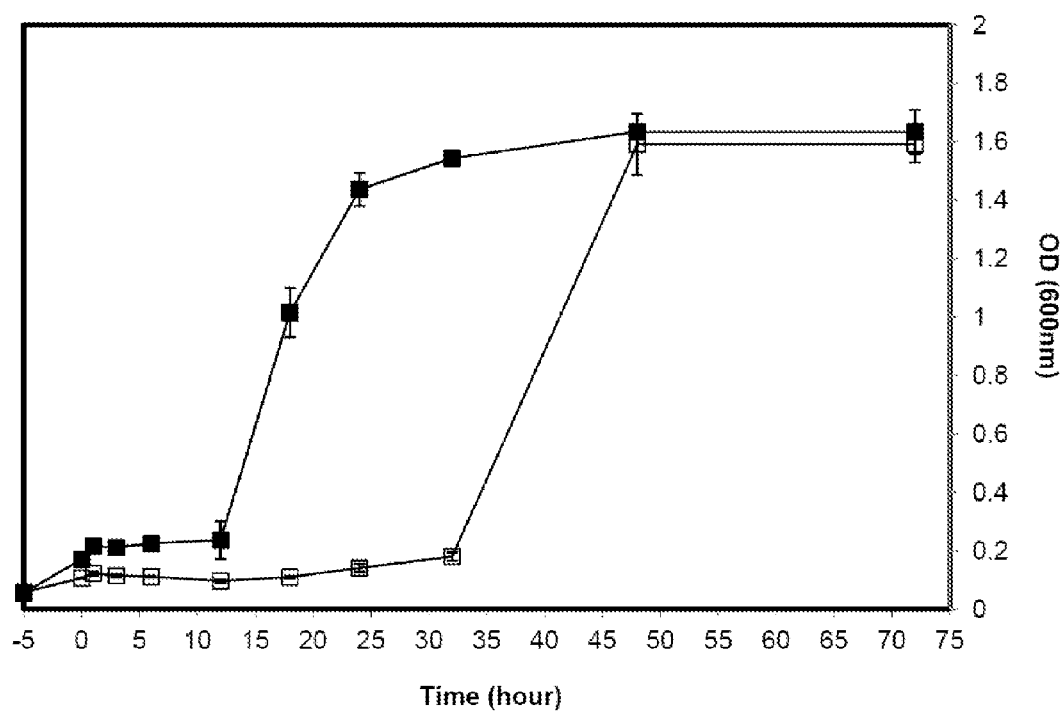
FIG. 1B is a graph depicting growth cell growth on a medium containing 15 mM each of furfural and 5-hydroxymethylfurfural between strain Y-50464 (filled square) and its parental wild type Y-417 (open square).
Figure 2A:
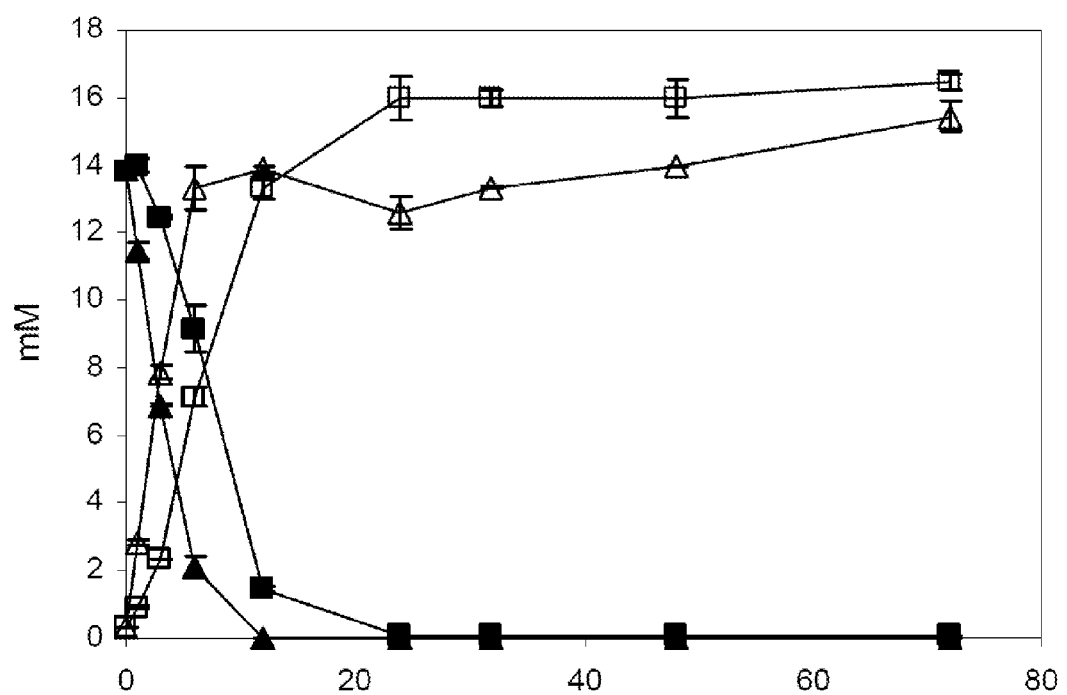
FIG. 2 is graph depicting the conversion of furfural (filled triangles) into FM (open triangles), and HMF (filled squares) into FDM (open triangles), for tolerant strain Y-50464 (A) and its parental wild type Y-417 (B) showing improved detoxification capability.
Figure 2B:
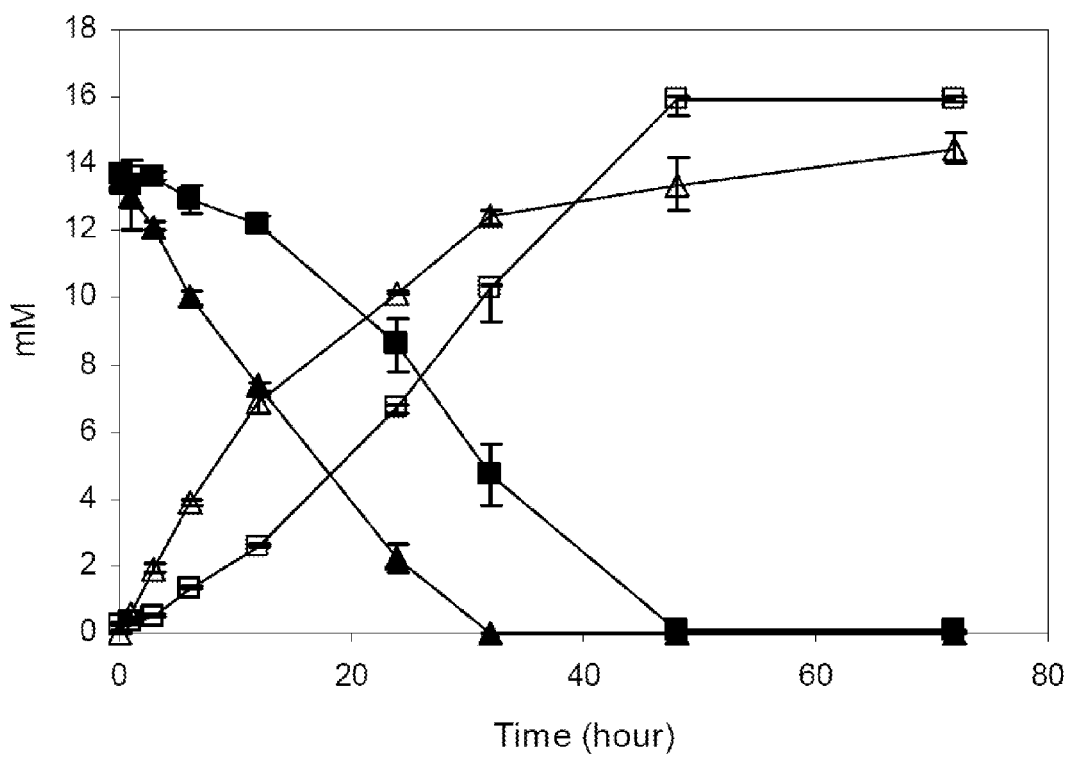

When growing on YP+ medium containing pretreatment inhibitors furfural and HMF (15 mM each), strain Y-50464 displayed significantly more tolerance to the inhibitor complex than that of its parental wild type Y-417. The obviously shorter lag phase did not appear to affect the cell growth and ethanol conversion significantly (FIGS. 1A and 1B). Strain Y-50464 reached the stationary phase at least 20 h in advance of Y-417 with complete sugar consumption and ethanol conversion. The ethanol fermentation was completed in less than 32 h in the presence of the inhibitor complex. The detoxification capability of Y-50464 in terms of conversion rate of furfural and HMF into less toxic furan methanol (FM) and furan-2,5-dimethanol (FDM) was also significantly improved compared with its parental wild type Y-417 (FIGS. 2A and 2B). In the inhibitor containing medium, the reduction rate of strain Y-50464 was two and five times faster than Y-417 over the first 12 h for furfural and HMF, respectively. Furfural was completely converted by Y-50464 into FM in no more than 12 h and HMF into FDM in less than 24 h compared to 32 h and 48 h respectively for Y-417.

Example 4

Ethanol Conversion with and without Addition of β-Glucosidase

Figure 3:
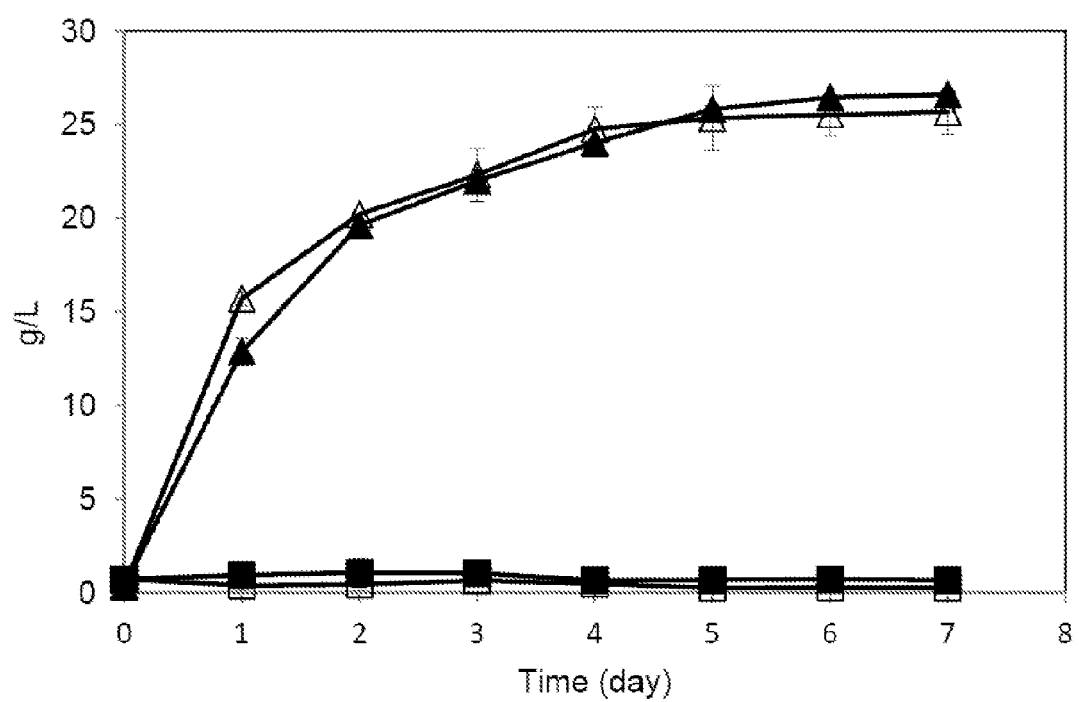
FIG. 3 is a graph depicting ethanol conversion from xylose-extracted corncob residues between strain Y-50464 with (open symbols) or without the addition (filled symbols) of β-glucosidase using a simultaneous saccharification and fermentation. Ethanol recovered by HPLC assay is labeled with a triangle and cellobiose residues by a square.

By conventional SSF practice of adding cellulase and β-glucosidase in a fermentation medium, strain Y-50464 reached its peak ethanol production of 25.7 g/L at day 5 (FIG. 3). Cellobiose remaining in the medium was at negligible levels at all time points especially toward the end of fermentation. Under the same conditions, *S. cerevisiae* Y-12632 showed a maximum ethanol production of 22.9 g/L at day 6 at 30° C., the optimized growth temperature for the yeast. A small amount of cellobiose was detected remaining in the medium was slightly higher than that observed for Y-50464.

Without the addition of β-glucosidase, strain Y-50464 produced 26.6 g/L ethanol from X-ER by SSF in 5 days with a minimum amount of cellobiose detected in the medium (FIG. 3). In contrast, without β-glucosidase, SSF by strain Y-12632 produced only 11.9 g/L ethanol at day 7. Approximately 10 g/L of cellobiose was detected remaining in the medium. The function of β-glucosidase is to digest cellobiose into the simple sugar glucose so that yeast is able to convert glucose into ethanol. A significant amount of cellobiose accumulation in the medium indicated the inability of *S. cerevisiae* Y-12632 to utilize cellobiose in the absence of β-glucosidase. However, without addition of β-glucosidase did not appear to affect cellobiose utilization and ethanol fermentation by strain Y-50464. As indicated by in vitro assay of crude cell protein extract, a significant amount of β-glucosidase enzyme activity was produced by cells of Y-50464 (Table 1). The amount of enzyme produced and the level of enzyme activity appeared sufficient for ethanol conversion from X-ER using SSF.

Comparisons of ethanol conversion from X-ER for strain Y-50464 and Y-12632 with or without addition of β-glucosidase (785 U/ml) were made by SSF procedures using 100 ml Nalgene culture bottles. Fermentations were performed using 20% solids loading with addition of a 10×YP+ medium to a final concentration of 50 ml 2×YP+ medium. Cellulase was added to all fermentation bottles at 0.15 ml/g of biomass. A treatment without the addition of β-glucosidase was conducted for each strain. All treatments were then inoculated with 5 g/L wet weight of cells and incubated with shaking at 250 rpm at 30° C. and 37° C. for strain Y-12632 and Y-50464 respectively.

Pretreatment of X-ER

Prior to the pretreatment, the X-ER was milled to a 1 mm particle size using a Model Thomas-Wiley Mill (Thomas Scientific, Swedesboro, N.J.). The milled substrate was weighed out to the desired final WIS (water insoluble) content. Dilute acid hydrolysis was applied to break down the cellulosic crystalline structure using 0.75% sulfuric acid at 160° C. for 10 minutes. The hydrolysate was then neutralized to a pH of 5.5 using 6N NaOH.

Example 5

Ethanol Conversion Efficiency

In order to compare with literature, ethanol conversion efficiency was calculated using traditional methods from SSF data of sealed bottle with varied X-ER loading concentrations of 15%, 25%, and 35%. The SSF was carried out with and without additional β-glucosidase (785 U/ml). In addition, a separate SSF experiment was carried out to estimate the conversion efficiency of soluble cellulose to ethanol from X-ER using a Standard Biomass Analytical Method provided by the National Renewable Energy Laboratory (Sluiter et al., 2008). The SSF using the above dilute acid pre-treated X-ER was conducted using 100 ml Nalgene culture bottles for 120 h. Each culture was inoculated with a 60 g/L (wet weight) overnight preculture of strain Y-50464. Varied concentrations of the solid substrate at 15%, 20%, and 25% (w/v) were used for this test. Celluclast 1.5 L was added at a concentration of 0.2 ml per gram of solids (dry weight). Cultures were incubated at 37° C. with agitation at 250 rpm. A sample of an unfermented pre-treated X-ER served as a control. Samples were analyzed for ethanol conversion by HPLC at the end of the fermentation. Samples of wet residue solids were taken and dried overnight at 50° C. After drying, a 0.3 g solid sample of each before and after fermentation was weighed out and placed into a test tube. Each tube was then filled with 3 ml of 72% H2SO4 (w/w) and mixed with a Teflon rod. The samples were then hydrolyzed by placing in a 30° C. water bath for 1 h and stirred every 10 min using a Teflon rod. The suspensions were diluted to 4% H2SO4 (w/w) by adding 84 ml of deionized water to each sample. The samples were then placed in a 100-ml serum bottle and capped with both a rubber and metal seal. The sealed samples were then autoclaved for 1 h at 120° C. and allowed to cool to room temperature. Then, 20 ml of supernatant was removed and neutralized with calcium carbonate to pH 7. Once the samples settled, supernatant was taken and used for HPLC analysis. Obtained results estimated the amount of total sugar prior to the fermentation and the remaining unhydrolyzed sugar at the end, and final ethanol concentrations were used to calculate the efficiency of ethanol conversion under each condition.

Figure 4:
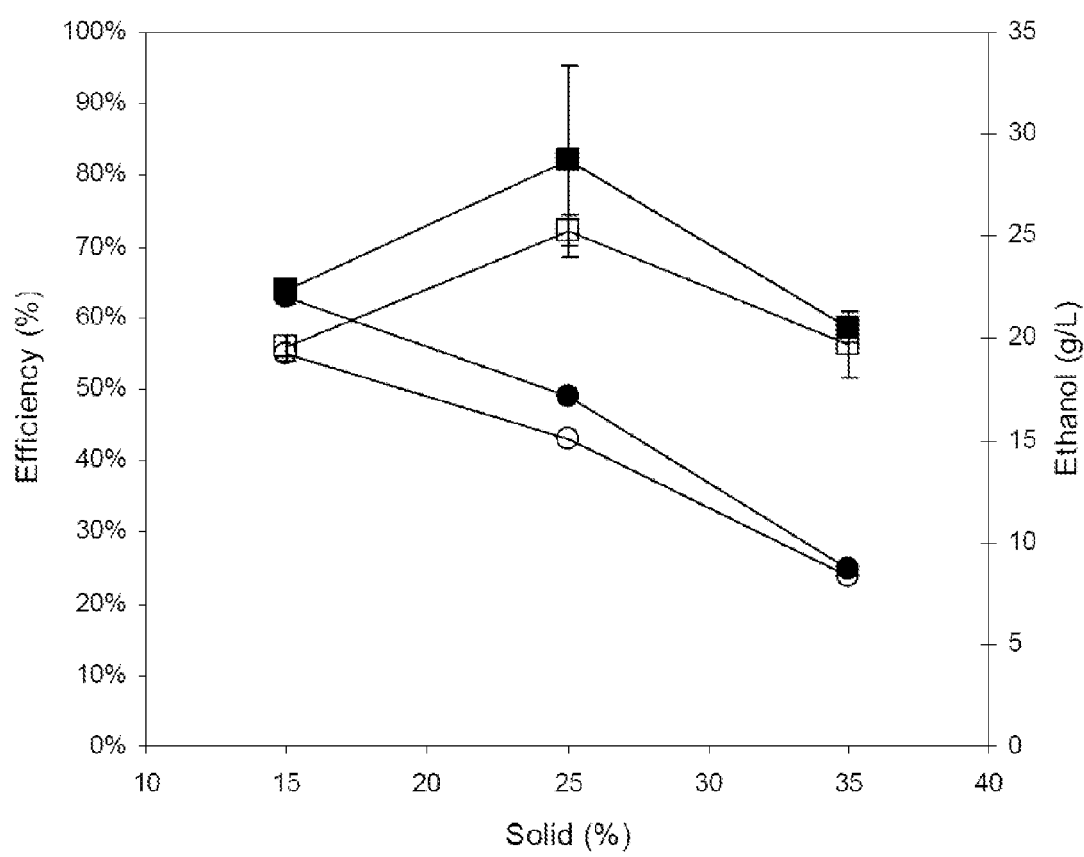
FIG. 4 is a graph depicting ethanol conversion yield (squares) and conversion efficiency (circles) using xylose-extracted corncob residues at 15, 25, and 35% solids loading by strain Y-50464 with (open symbols) and without (filled symbols) the addition of β-glucosidase in simultaneous saccharification and fermentation.

The traditional conversion efficiency was calculated assuming all cellulose is available to be converted to glucose and further to ethanol. Using this method, the conversion efficiency with added β-glucosidase was 55, 43, and 24% for 15, 25, and 35% solids loading, respectively (FIG. 4). As cellulosic biomass loading levels increased, efficiency of ethanol conversion (% of theoretical yield) decreased with a near linear relationship whether β-glucosidase was added or not. The highest level of ethanol production at 28.7 g/L was observed at 25% solids loading followed by 15% with 22.3 g/L of ethanol produced. Solids loading of 35% produced the lowest level of ethanol. Ethanol conversion efficiency using corncobs was previously observed at 53% for 15% solids loading (Latif and Rajoka, 2001). The conversion efficiency of X-ER observed in this study of 55% seemed comparable with that of corncobs. However, these estimates are based on a complete cellulose conversion and may not reflect a realistic situation in cellulose SSF.

When Y-50464 was used in fermentation without the addition of β-glucosidase, ethanol production was significantly increased at 15 and 25% solids loading levels compared with the addition of β-glucosidase treatment for the same solids loadings (FIG. 4). Accordingly, the conversion efficiency was also increased to 63% and 49% for 15% and 25% solids loading levels, respectively. This was almost an 8% increase of efficiency compared with the additional β-glucosidase. The extra expense of additional β-glucosidase in fact did not add any benefits to ethanol production compared with no enzyme addition treatment in this study, especially at 15 and 25% solids loading levels. Since Y-50464 produces its own β-glucosidase, artificially overdosing the enzyme could to interfere with the conversion process. Results indicate that the Y-50464 appeared able to complete cellobiose fermentation on its own.

Using a recently established standard biomass analytical method (Sluiter et al., 2008), additional assays were performed to evaluate the glucose to ethanol conversion efficiency of the strain by analyzing total available glucose in the biomass just prior to SSF and after SSF. By doing this, it is possible to determine the amount of glucose that remained insoluble and base sugar conversion efficiency on glucose consumed by the strain rather than total cellulosic glucose which includes the insoluble fraction. Such results indicated that between solids loading levels from 15 to 25%, the glucose consumed increased with the highest consumed glucose at 77.36 g/L for 25% and 53.98 g/L for 15% solids loading (Table 2). Ethanol production also increased with the increasing solids loading levels, although it was not a linear relationship. As expected, the higher glucose to ethanol conversion efficiency was observed for the lower solids loading level at 15% (Table 2). However, the effect of higher solids loading on conversion efficiency is more obvious than lower solids loading levels. For example, an approximate 13% decrease in efficiency was observed as the solid was increased from 15% to 20% but only about a 3% decrease when it was increased from 20% to 25% loading levels. A significant portion of insoluble sugar remained unavailable for yeast fermentation, especially for higher load level such as 25%.

TABLE 2

Efficiency of ethanol conversion by strain Y-50464 from consumed X-ER glucose using SSF

| Solid load (%) | X-ER biomass (g/L) | Cellulose content (g/L) | Glucose consumed (g/L) | Theoretical ethanol yield (g/L) | Measured ethanol yield (g/L) | Efficiency (% of theoretical yield) |
|---|---|---|---|---|---|---|
| 15 | 150 | 67.05 | 53.98 | 26.99 | 25.0 | 93 |
| 20 | 200 | 89.4 | 70.51 | 35.26 | 27.9 | 79 |
| 25 | 250 | 111.75 | 77.36 | 38.68 | 29.3 | 76 |

Example 6

Ethanol Production from Xylose Extracted Corncob Residues

Fermentation experiments were carried out using 1 L 2×YP+ media in a 2-L bioreactor (Sartorius Stedim Biotech, Aubagne Cedex, France). For SSF bioreactor fermentation experiments, no additional glucose was added in the substrate. Xylose-extracted corncob residue (X-ER) was kindly supplied by Longlive Co., Ltd. (Yucheng, Shandong, China) and stored dry at room temperature until use.

SSF was carried out on YP+ medium contain additional nutrients of 2.0 g $KH_2PO_4$, 1 g $(NH4)_2SO_4$, 0.5 g $MgSO_4.7H_2O$, 0.1 g NaCl, and 1.0 ml of a trace mineral solution per liter. The trace mineral solution consisted of 0.25 g $CuSO_4.5H_2O$, 0.169 g $MnSO_4.H_2O$, 0.287 g $ZnSO_4.7H_2O$, 0.238 g $CoCL_2 6H_2O$, 3 drops $H_2SO_4$ (18N) in 100 ml of distilled water and was filter sterilized.

Figure 5A:
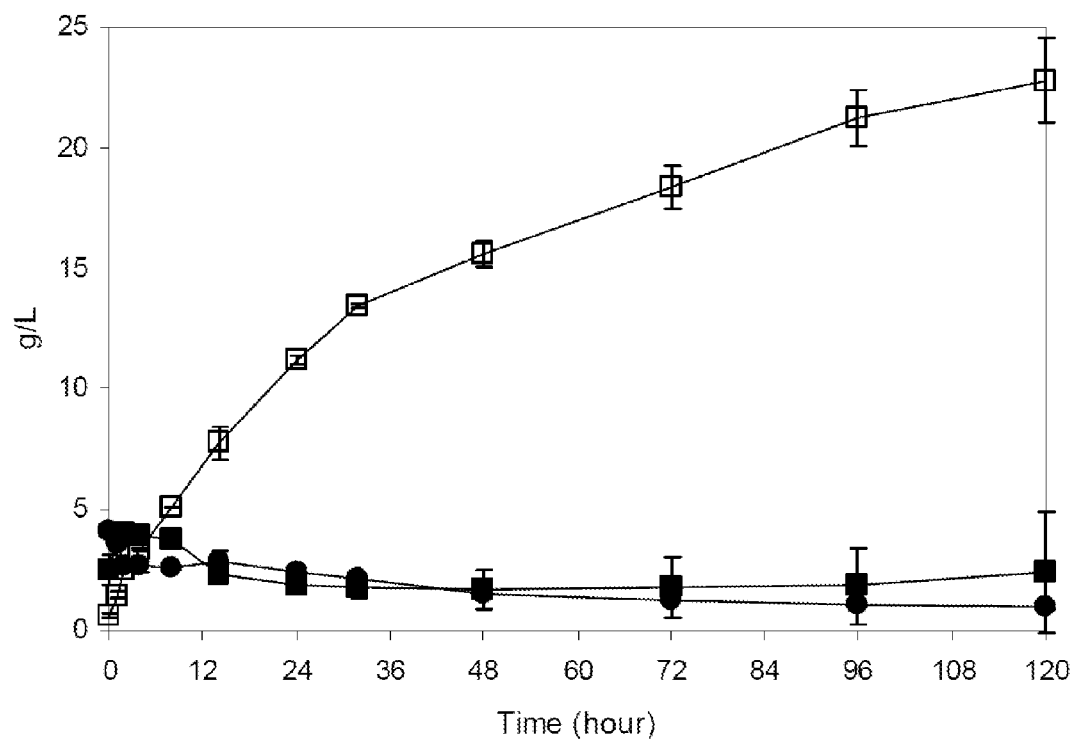
FIGS. 5A and 5B are graphs depicting cellulosic ethanol production by strain Y-50464.
Figure 5B:
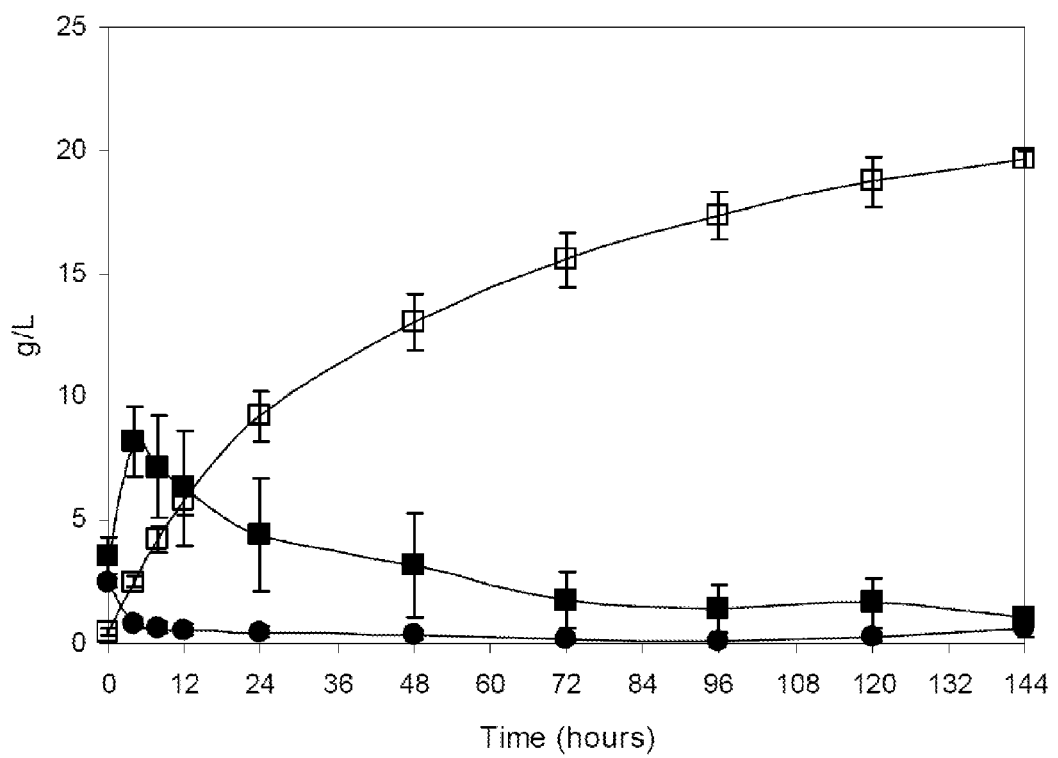

Applying SSF procedures with cellulase and without addition of β-glucosidase using 2-L bioreactors, ethanol was produced at 23 g/L in 5 days (FIG. 5A) with a 25% solids loading. With a 20% solids loading, ethanol production was 20 g/L in 6 days (FIG. 5B). In these fermentations, available glucose was quickly consumed while cellobiose reached its peak level at 4 h. After day 3, cellobiose levels appeared stabilized, however, ethanol production continually increased. This indicated additional ethanol conversion from glucose that released from cellobiose by β-glucosidase. At the end, a negligible amount of sugars was detected remaining in the medium. A high inoculum level of 60 g/L did not reduce the entire fermentation time needed to utilize all cellulose. In contrast, for lower inoculum level at 5 g/L for SSF with a 25% solids loading, the ethanol production was increased more consistently over time. The concentration of ethanol produced was higher and the fermentation time was one day shorter. It seemed the yeast inoculum level may not be critical and a large inoculum is not necessary for SSF by Y-50464.

The X-ER contains approximately 66.56% (w/w %, g/100 g) acid detergent fiber and 65.10% neutral detergent fiber based on analysis from the University of Missouri. This indicated a negative content of hemicelluloses calculated by the difference of the two fibers. Since X-ER was processed previously for xylose production, most available hemicelluloses are expected to be consumed. X-ER contained 44.77% cellulose followed by 14.02% lignin and 31.48% ash. The cellulose amount was close to a previous estimate of cellulose content at 49% for the X-ER (Zhang et al., 2011). It is apparent that after xylose extraction, abundant cellulose remains in the residue that can be utilized for cellulosic ethanol conversion.

SSF of X-ER for ethanol production was carried out in a 2 liter bioreactor using the acid-pretreated solids. Pretreated X-ER was diluted to a final WIS concentration of 25% or 20% (dry weight) using a 10×YM+ medium to a final concentration of 2× as described above. All reactors were then autoclaved for complete sterilization. The fermentors were maintained at 37° C. with agitation at 350 rpm. To each bioreactor, an overnight culture of Y-50464 at 5 g/L for 25% solid or 60 g/L (wet weight) for 20% solid was added along with Celluclast 1.5 L (Cellulase 34±2 FPU) at a concentration of 0.2 ml per gram of X-ER. Samples were taken periodically for HPLC analysis. Each fermentation experiment was run in triplicate.

While the invention has been described with reference to details of the illustrated embodiment, these details are not intended to limit the scope of the invention as defined in the appended claims. The embodiment of the invention in which exclusive property or privilege is claimed is defined as follows:

The invention claimed is:

1. An isolated *Clavispora* spp. having been deposited with the United States Department of Agriculture, Agricultural Research Patent Culture Collection as Accession Deposit Number NRRL Y-50464.

2. The *Clavispora* spp. of claim 1 wherein the yeast strain metabolizes cellobiose and produces ethanol.

3. The *Clavispora* spp. of claim 1 wherein the yeast strain produces beta-glucosidase when fermenting cellobiose.

4. A method of producing ethanol from the fermentation of cellulosic material comprising:
 fermenting the yeast strain of claim 1 with cellulosic material under suitable conditions for a period of time sufficient to allow fermentation of at least a portion of cellulosic material to ethanol.

5. The method as described in claim 4 further comprising contacting the cellulosic material is contacted with β-glucosidase produced by the yeast strain of claim 1 and adding cellulase to the cellulosic material for simultaneous saccharification and fermentation.

6. The method as described in claim 4 wherein said cellulosic material comprises a lignocellulosic biomass.

7. The method as described in claim 5 further comprising subjecting said lignocellulosic biomass to a pretreatment to increase the accessible surface area of cellulose, prior to said contacting with said cellulase and said β-glucosidase.

8. The method as described in claim 7 wherein said pretreatment is selected from the group consisting of treatment with acid, treatment with alkali, ammonia fiber explosion, treatment with an organic solvent, autohydrolysis by steam explosion, acid steam treatment, treatment with hot, compressed liquid water, pressure cooking, milling, grinding, shearing, and extruding.

9. The method as described in claim 7 wherein said lignocellulosic material is selected from the group consisting of agricultural residues, wood, municipal solid wastes, paper and pulp industry wastes, and herbaceous crops.

10. The method of claim 7 wherein the lignocellulosic material is xylose-extracted corncob residue.

11. The method as described in claim 4 further comprising fermenting said glucose to ethanol.

12. The method as described in claim 11 wherein the conversion of said cellulosic material to glucose and the fermentation of glucose to ethanol are conducted simultaneously.

13. The method as described in claim 11 wherein the conversion of said cellulosic material to glucose and the fermentation of glucose to ethanol are conducted sequentially.

* * * * *